United States Patent
Schmitt et al.

(10) Patent No.: US 7,539,529 B2
(45) Date of Patent: May 26, 2009

(54) APPARATUS FOR ANGIOGRAPHIC X-RAY PHOTOGRAPHY

(75) Inventors: Holger Schmitt, Los Angeles, CA (US); Michael Grass, Buchholz in der Nordheide (DE); Volker Rasche, Wellesley, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 214 days.

(21) Appl. No.: 10/553,770

(22) PCT Filed: Apr. 21, 2004

(86) PCT No.: PCT/IB2004/050476

§ 371 (c)(1), (2), (4) Date: Jun. 19, 2006

(87) PCT Pub. No.: WO2004/093684

PCT Pub. Date: Nov. 4, 2004

(65) Prior Publication Data

US 2006/0293579 A1    Dec. 28, 2006

(30) Foreign Application Priority Data

Apr. 22, 2003    (EP)    ................................ 03101103

(51) Int. Cl.
*A61B 6/00* (2006.01)
*A61B 6/02* (2006.01)

(52) U.S. Cl. ............................ 600/431; 600/428; 378/4; 378/62

(58) Field of Classification Search ................ 600/465, 600/419, 420, 431; 128/2
See application file for complete search history.

(56) References Cited

U.S. PATENT DOCUMENTS 4,037,585 A    7/1977    Gildenberg (Continued)

FOREIGN PATENT DOCUMENTS

DE    38 26 550 C2    2/1989

(Continued)

OTHER PUBLICATIONS

Wahle, A., et al.; Four-dimensional coronary morphology and computational hemodynamcis; 2001; Proc. of SPIE; 4322:743-754.

*Primary Examiner*—Eric F Winakur
*Assistant Examiner*—Helene Bor

(57) ABSTRACT

The invention relates to an X-ray imaging device for visualizing the blood flow in a coronary vascular tree of a patient. According to the invention a first set (1) of X-ray projection images of the vascular tree is recorded during various phases of the heart cycle with simultaneous recording of the ECG (2) of the patient. By means of a suitable program control, computer means (17) of the device according to the invention a reconstruction then follows of the three-dimensional structure of the vascular tree during the various phases of the heart cycle. The invention proposes, to determine the time-dependent concentration of contrast agent within the reconstructed three-dimensional structure of the vascular tree, that local image areas within the X-ray projection images of the second set (6) assigned to individual vascular segments (5, 8) are located in accordance with the spatial positions of the vascular segments (5, 8) in the relevant phase of the heart cycle. The concentration of contrast agent in the area of the vascular segments (5, 8) is then determined by evaluation of the X-ray absorption within the local image areas found.

11 Claims, 2 Drawing Sheets

U.S. PATENT DOCUMENTS

| | | | |
|---|---|---|---|
| 5,852,646 A * | 12/1998 | Klotz et al. | 378/8 |
| 6,148,095 A | 11/2000 | Prause et al. | |
| 6,366,635 B1 * | 4/2002 | Op De Beek et al. | 378/4 |
| 6,442,235 B2 * | 8/2002 | Koppe et al. | 378/62 |
| 6,801,800 B2 * | 10/2004 | Miyazaki et al. | 600/410 |
| 6,818,199 B1 * | 11/2004 | Hainfeld et al. | 424/1.11 |
| 6,823,204 B2 * | 11/2004 | Grass et al. | 600/407 |
| 6,959,067 B2 * | 10/2005 | Rasche et al. | 378/8 |
| 7,180,976 B2 * | 2/2007 | Wink et al. | 378/8 |
| 2002/0045820 A1 * | 4/2002 | Pesque | 600/443 |
| 2002/0087069 A1 * | 7/2002 | Ho et al. | 600/415 |
| 2003/0074011 A1 * | 4/2003 | Gilboa et al. | 606/130 |
| 2003/0078500 A1 * | 4/2003 | Evron et al. | 600/443 |
| 2004/0097805 A1 * | 5/2004 | Verard et al. | 600/428 |
| 2006/0188138 A1 * | 8/2006 | Kohler et al. | 382/130 |
| 2006/0210134 A1 * | 9/2006 | Grass et al. | 382/130 |
| 2007/0016108 A1 * | 1/2007 | Camus et al. | 600/587 |

FOREIGN PATENT DOCUMENTS

| | | | |
|---|---|---|---|
| DE | 101 19 228 A1 | | 12/2002 |
| DK | WO 00/57777 | * | 3/2000 |
| EP | 0 362 821 A1 | | 4/1990 |
| EP | 1 114 615 A2 | | 7/2001 |

* cited by examiner

APPARATUS FOR ANGIOGRAPHIC X-RAY PHOTOGRAPHY

The invention relates to an X-ray imaging device with computer means which are arranged for visualizing the blood flow in a coronary vascular tree of a patient.

The invention also relates to a corresponding computer program as well as an X-ray imaging method which can be implemented on the device according to the invention.

In the field of angiography, three-dimensional medical imaging methods, such as three-dimensional rotation X-ray imaging (3D-RX), are increasing in importance. The image data obtained with such methods contains interesting information for the diagnosis of vascular diseases such as e.g. stenosis. The visualization of the vascular structures is then decisive, so that an attending doctor can rapidly and reliably recognize potential sources of problems.

Methods are known in the state of the art that allow the three-dimensional structure, formed from numerous two-dimensional projected images taken by 3D-RX of a vascular tree to be examined, to be reconstructed on a suitable computer using special modeling or back-projection techniques. The computer-aided three-dimensional reconstruction of the patient's vascular tree from the recorded imaging data thus allows the visualization of the behavior of the vascular system with high reproduction accuracy, where anatomical structures not related to the vascular system of interest can be eliminated where necessary. The three-dimensional reconstruction of the vascular structures is in particular a useful tool for the planning of interventions such as, for instance, left ventricular catheter examinations (PTCA).

However, in the methods as yet known, the disadvantage is that no information is obtained regarding the blood flow through the examined vascular tree. The flow behavior and, in particular, the flow speed of the blood could be important aspects for the examining doctor with regard, for instance, to the level of severity of an existing stenosis. The known methods allow the doctor to evaluate the condition of a stenosis solely from the reconstructed geometry of the vascular system. It is, however, not possible with the known methods, which only provide static images of the vascular tree, to estimate the seriousness of a stenosis based on the effect of said stenosis on the blood flow, i.e. the flow speed of the blood in the area of the stenosis.

Therefore it is an object of the invention to develop an X-ray imaging device that allows the flow behavior of the blood in the coronary vascular tree to be examined.

The object of the invention is achieved by a device according to claim 1.

The invention is based on the use of a suitable computer of an X-ray imaging device for visualizing the blood flow in a coronary vascular tree. Within the context of the invention the claimed X-ray imaging device may be a complete X-ray device with corresponding image recording means or also a single workstation for processing medical image data.

The invention proposes for the visualization that a data set is started from consisting of X-ray projection images and ECG data (electrocardiogram) derived therefrom in parallel of the examined patient. These data may be included in the approach to the visualization and then be fed to the computer via a corresponding data input or via buffering in a database. This procedure occurs when the technique according to the invention is used on a medical workstation separate from the device used for the actual image recording. Alternatively, the data can already be processed during the image recording according to the invention when the computer means used for this purpose are directly assigned to the respective imaging means.

Accordingly, a first set of X-ray projection images of the vascular tree is recorded in various phases of the heart cycle, preferably from different directions of projection. In order to visualize the vascular tree in the X-ray projection images, a suitable contrast agent is administered to the patient. During the recording of the first set of X-ray projection images also the patient's ECG is continuously recorded, so that each of the recorded images can be assigned to a certain phase of the heart cycle.

Based on the first set of X-ray projection images, the three-dimensional structure of the vascular tree during the various phases of the heart cycle is first reconstructed using a method known per se. The reconstructed structure is then divided into a number of vascular segments where the flow behavior of the blood can be examined individually.

During or immediately after the administering of a contrast agent, a second set of X-ray projection images of the vascular tree is recorded—again with simultaneous recording of the patient's ECG. To record the second set of X-ray projection images, only a short contrast agent bolus is administered for this purpose, this being an advantage for the examination of the blood flow behavior according to the subsequent method steps described below. The recording of the first set of X-ray projection images is preferably implemented with a longer contrast agent bolus, so that the three-dimensional structure of the vascular tree can be examined as precisely as possible.

The flow behavior of the blood in the vascular tree can then be examined by determining the time-dependent concentration of contrast agent within the reconstructed three-dimensional structure of the vascular tree. According to the invention, the second set of X-ray projection images is assigned to a respective phase of the heart cycle using the recorded ECGs. Local image areas within the X-ray projection images of the second set are then discovered for the vascular segments of the reconstructed structure of the vascular tree, particularly corresponding to the spatial positions of these vascular segments in the relevant phase of the heart cycle. For this purpose the projection angles at which the second set of X-ray projection images was taken can be used to calculate the image areas where the respective vascular segments are imaged in the respective projection images. By evaluating the X-ray absorption within the image areas generated in this manner, it is then determined how the concentration of contrast agent within the individual vascular segments changes over time, i.e. how the vascular tree is filled with contrast agent. This allows immediate conclusions to be made about the flow behavior of the blood within the vascular tree.

The contrast agent flow determined in accordance with the method described previously must then be suitably visualized to the examining doctor. For this purpose it is possible, for example, for the time-dependent concentration of contrast agent to be presented as a brightness or color value in a three-dimensional display of the reconstructed three-dimensional structure of the vascular tree.

The basic idea of the invention is to take into account the movements of the blood vessels during the heartbeat activity for the reconstruction of the three-dimensional structure of the vascular tree. Not only is the structure itself reconstructed, but also the change over time caused by the movement of the heart. The assignment of the individual movement stages of the vascular tree to the respective phases of the heart cycle is implemented using the ECGs recorded in parallel with the image recording. In addition, the idea of the invention is to record the patient's ECG during the recording of the second set of X-ray projection images so that, with reference to the respective phase of the heart cycle, the reconstructed three-dimensional structure of the vascular tree can be correlated with the image characteristics of the second set of X-ray projection images. This results in fully comprehensive three-dimensional data of how the blood flows through the vascular tree.

It is possible in a particularly advantageous manner to initially record the second set of X-ray projection images during or after the administration of the contrast agent, while the vascular tree fills with contrast agent, and then to take the first set of X-ray projection images after the vascular tree is completely filled with contrast agent. In this manner, only a single dose of contrast agent needs to be administered. The evaluation of the X-ray projection images as described above for the determination and visualization of the time-dependent concentration of contrast agent within the vascular tree is then effected by the computer means of the X-ray image recording device once the image recording of the first and second sets of X-ray projection images is complete.

If portions of the vascular tree run in the projection direction when the X-ray projection images are recorded, or if portions of the vascular tree cover each other in the projection direction, it is not possible to clearly assign the vascular segments concerned to the respective image areas. It is therefore expedient for the recording of the first and/or second set of X-ray projection images to be made by continuous rotation-X-ray imaging at multiple projection angles.

It must be noted that the recording of the first set of X-ray projection images should be effected from as many projection directions as possible, so that the three-dimensional spatial structure of the vascular tree is reconstructed as precisely as possible. Reconstruction can particularly take place based on numerous projection images taken during several consecutive heart cycles. In contrast, for the recording of the second set of X-ray projection images, particular attention should be paid to the resolution over time, so that the flow of the contrast agent into the vascular tree can be precisely followed. It is therefore useful to use the recording of the second set of X-ray projection images from only a few or even just one fixed projection angle.

Therefore, the recording of the first set of X-ray projection images expediently takes place under continuous rotation-X-ray imaging during several consecutive heart cycles and the second set takes place at only few, if necessary fixed, projection angles with the highest possible resolution over time, while the vascular tree fills with contrast agent.

In addition to the vascular tree, the three-dimensional image derived and reconstructed from the first set of X-ray projection images may also depict anatomical structures, for instance bones, which can be an interference factor in further evaluations. It is therefore useful to use computer-aided modeling of the vascular tree while eliminating the anatomical structures contained in the first set of X-ray projection images for the reconstruction of the three-dimensional structure of the vascular tree.

A computer program according to claim 7 is suitable for the implementation of the visualization technique according to the invention on an X-ray imaging device equipped with a suitable computer means. The relevant software can be rendered available to the users of suitable imaging devices, preferably on a data carrier such as a floppy disk or CD-ROM, or as a download via a data network (Internet).

An X-ray imaging method, which can be implemented on the device according to the invention forms subject matter of the patent claims 8 to 11.

These and other aspects of the invention are apparent from and will be elucidated with reference to the embodiments described hereinafter. In the drawings.

Figure 1:
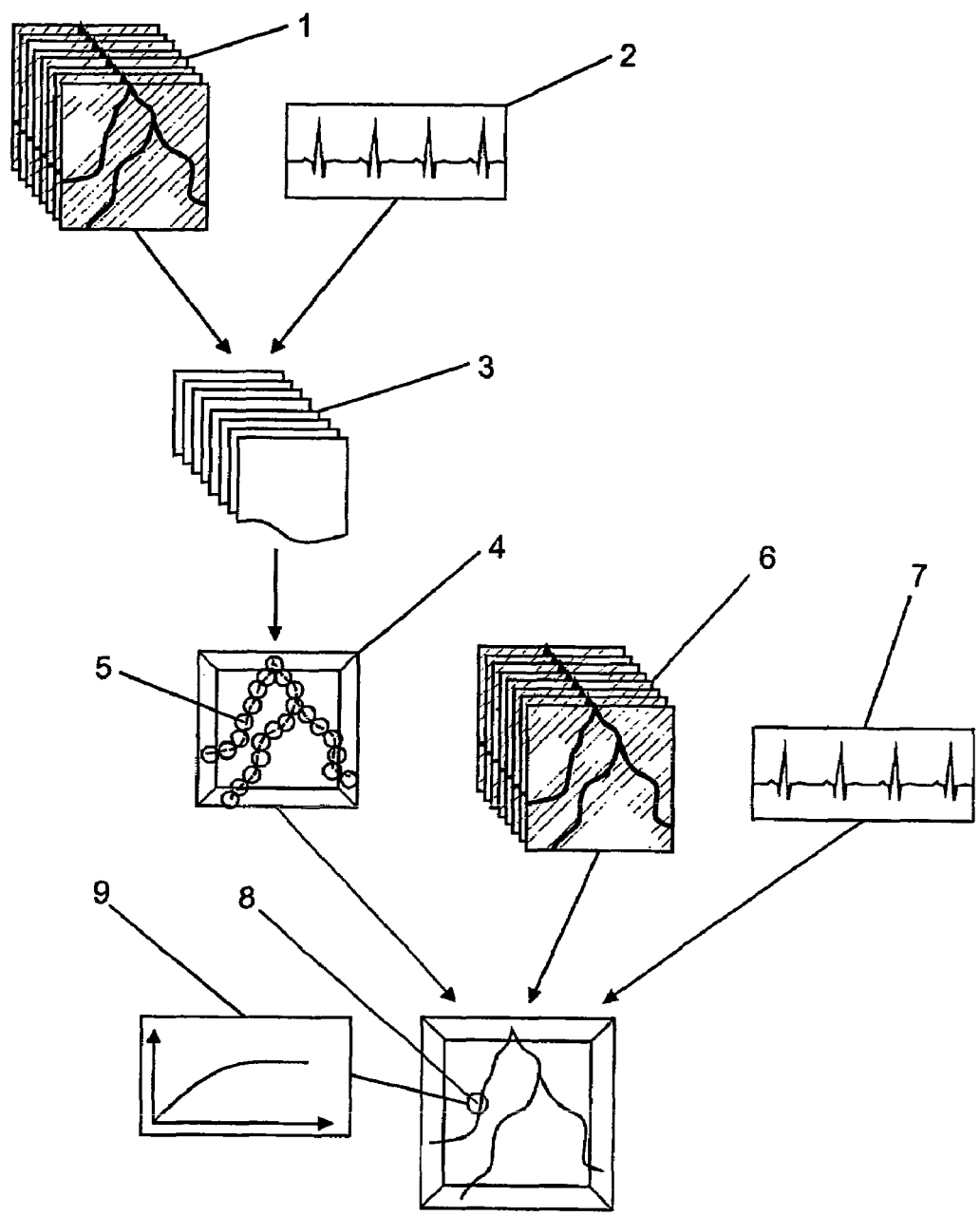
FIG. 1 Shows a flow chart of the visualization technique according to the invention.

The method schematically depicted in FIG. 1 is used to visualize the blood flow in a coronary vascular tree of a patient. The method begins with the recording of a first set 1 of X-ray projection images during various phases of the heart cycle. In parallel with the recording of the X-ray projection images, a first ECG 2 of the patient is recorded. The first set 1 of X-ray projection images is first used to reconstruct the three-dimensional structure of the vascular tree in the various phases of the heart cycle, so that, subsequently, a set 3 of three-dimensional data records is available of the coronary vascular structure for the various phases of the heartbeat. This is followed by computer-aided modeling of the vascular tree, where anatomical structures contained in the X-ray projection images that are not part of the vascular tree under examination are eliminated. The three-dimensional structure of the vascular tree in a data record 4 is split up into a number of vascular segments 5. The data record 4 contains information about the spatial position of each vascular segment 5 in every phase of the heart cycle, so that the structure and movement of the vascular tree is fully modeled by the data record 4.

In the further course of the method a second set 6 of X-ray projection images of the vascular tree is recorded during or after the administration of a contrast agent. A second ECG 7 of the patient is also recorded then. The X-ray projection images of the second set 6 are respectively assigned to a phase of the heart cycle using the ECG 7.

For a vascular segment 8 for which the time-dependence of the concentration of contrast agent is to be determined, local image areas are found within the X-ray projection images of the second set 6 in accordance with the spatial position of the vascular segment 8 in a specific phase of the heart cycle. The time-dependent position data in data record 4 are used for this purpose. The concentration of contrast agent within the vascular segment 8 is then determined by evaluating the X-ray absorption within the located local image area. The time curve of the concentration of contrast agent in the area of the vascular segment 8 can for be depicted as graph 9 the purpose of visualization. Such graphs can be created for all vascular segments, resulting in an overall comprehensive picture of the blood flow within the vascular tree.

Figure 2:
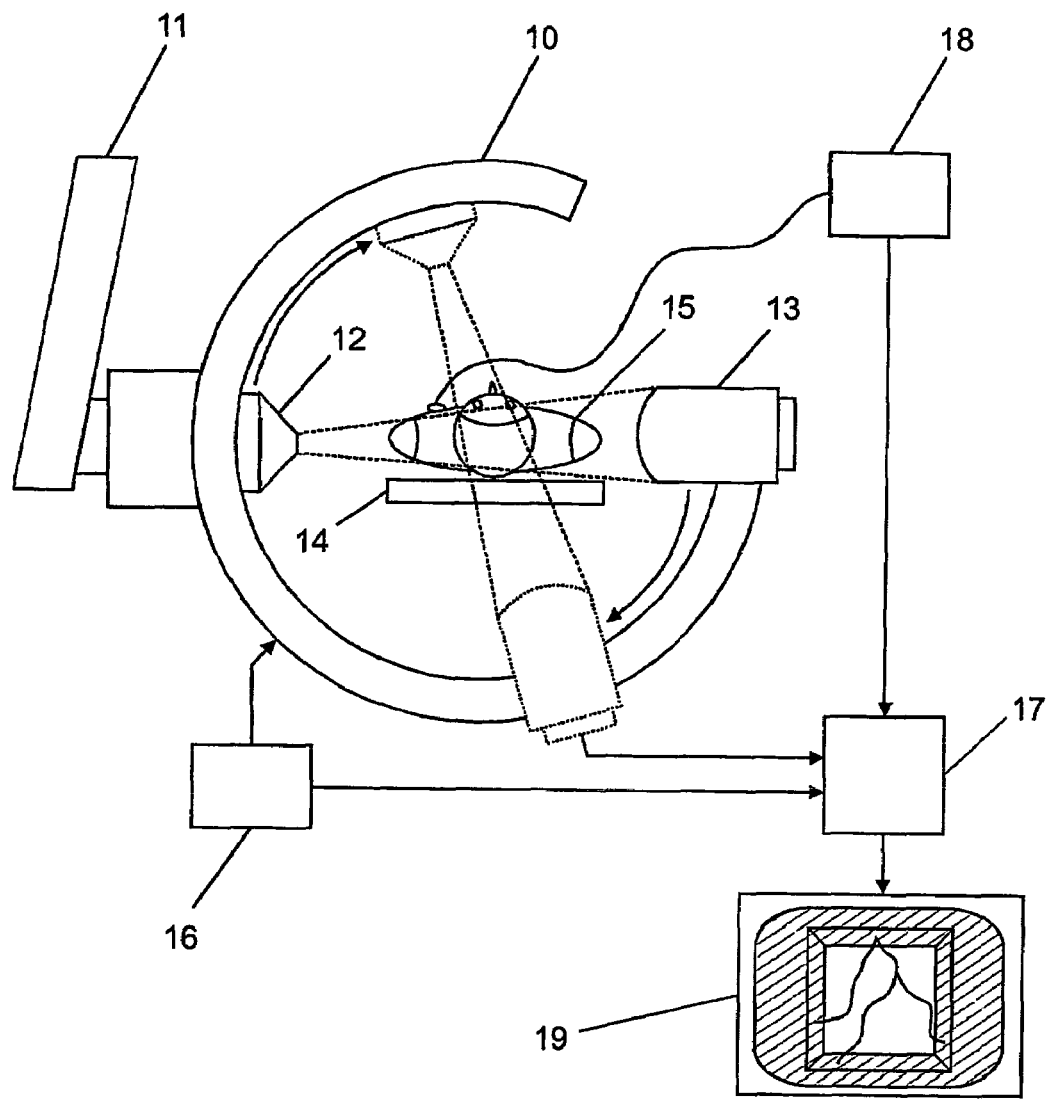
FIG. 2 shows an X-ray imaging device according to the invention.

The imaging device shown in FIG. 2 is a C-Arm X-ray device, which has a C-Arm 10, suspended from a ceiling (not shown) by means of a holder 11. The C-Arm 10 is equipped with a moveable X-ray radiation source 12 and an X-ray image converter 13, so that a number of X-ray projection images can be taken of a patient 15 lying on the patient table 14 in the center of the C-Arm 10 from various projection angles. The synchronous movement of the X-ray radiation source 12 and the X-ray image converter 13 is controlled by a control unit 16. During image recording, the X-ray radiation source 12 and the X-ray image converter 13 move synchronously around the patient 15. The image signals generated here by the X-ray image converter 13 are transmitted to a computer-controlled image processing device 17. The patient's heartbeat is monitored by an ECG device 18 and the ECG is transmitted to the image processing device 17. The image processing device 17 has a program control by which the X-ray projection images are processed according to the method described above. A monitor 19 connected to the image processing device 17 is used for visualization.

The invention claimed is:

1. An X-ray imaging device with an image processing device which is provided for visualizing blood flow in a coronary vascular tree of a patient such that the visualization is effected based on data which contain a first set of X-ray projection images of the vascular tree in various phases of a heart cycle, a first ECG of the patient recorded simultaneously with the first set, a second set of X-ray projection images recorded during or after administration of a contrast agent and a second ECG of the patient recorded simultaneously with the second set, wherein the image processing device comprises a program control which operates in accordance with the following method steps for determining a time-dependent concentration of the contrast agent within a three-dimensional structure of the vascular tree:

reconstructing the three-dimensional structure of the vascular tree during the various phases of the heart cycle using the first set of X-ray projection images and splitting of the structure into a number of vascular segments;

determining the time-dependent concentration of the contrast agent within the reconstructed three-dimensional structure of the vascular tree by a) assigning the second set of X-ray projection images to a respective phase of the heart cycle using the recorded second ECG;

b) finding local image areas assigned to the vascular segments within the second set of X-ray projection images corresponding to spatial positions of the vascular segments in the respective phase of the heart cycle according to the three-dimensional structure of the vascular tree;

c) determining the concentration of the contrast agent within the vascular segments by evaluating an X-ray absorption within the local image areas found in the method step b); and generating a visualization of flow of the contrast agent through the three-dimensional structure of the vascular tree according to the time-dependent concentration of contrast agent: wherein the recording of the first and second set of X-ray projection images is effected at a plurality of projection angles.

2. The X-ray imaging device as claimed in claim 1, wherein the second set of X-ray projection images is recorded during or after the administration of the contrast agent, while the vascular tree fills with the contrast agent and then the first set of X-ray projection images is recorded after the vascular tree is completely filled with the contrast agent.

3. The X-ray imaging device as claimed in claim 1, further comprising means for generating the first and the second set of X-ray projection images of the coronary vascular tree of the patient under various projection directions and means for recording the ECG of the patient during the recording of the first and second sets of X-ray projection images.

4. The X-ray imaging device as claimed in claim 2, wherein the image processing device is arranged such that during or after the administration of the contrast agent the second set of X-ray projection images is recorded while the vascular tree fills with contrast agent, and subsequently the first set of X-ray projection images is recorded, after which the vascular tree completely fills with the contrast agent.

5. The X-ray imaging device as claimed in claim 2, wherein the image processing device is further arranged such that the recording of the first and second set of X-ray projection images at the plurality of projection angles is by means of continuous rotation X-ray imaging.

6. The X-ray imaging device as claimed in claim 1, wherein the image processing device is arranged such that reconstructing the three-dimensional structure of a computer-aided modeling of the vascular tree is effected while eliminating the other anatomical structures contained in the first set of X-ray projection images.

7. A computer readable medium comprising a computer program for an X-ray imaging device for visualization of the blood flow in a coronary vascular tree of a patient, wherein the computer program receives as input variables data which contain a first set of X-ray projection images of the vascular tree in various phases of a heart cycle, a first ECG of the patient recorded simultaneously with the first set, a second set of X-ray projection images recorded during or after the administration of a contrast agent and a second ECG of the patient recorded simultaneously with the second set, wherein an image processing device when executing the computer program operates in accordance with the following method steps for determining a time-dependent concentration of the contrast agent within a three-dimensional structure of the vascular tree:

reconstructing the three-dimensional structure of the vascular tree during the various phases of the heart cycle using the first set of X-ray projection images and splitting of the structure into a number of vascular segments;

determining the time-dependent concentration of the contrast agent within the reconstructed three-dimensional structure of the vascular tree by a) assigning the X-ray projection images of the second set to a respective phase of the heart cycle using the recorded second ECG;

b) finding local image areas assigned to the vascular segments within the X-ray projection images of the second set that correspond to spatial positions of the vascular segments in the respective phase of the heart cycle according to the three-dimensional structure of the vascular tree;

c) determining the concentration of the contrast agent within the vascular segments by evaluating an X-ray absorption within the local image areas found in the method step b); and generating a visualization of flow of the contrast agent through the three-dimensional structure of the vascular tree according to the time-dependent concentration of the contrast agent wherein the recording of the first and second set of X-ray projection images is effected at a plurality of projection angles.

8. An X-ray imaging method for visualizing blood flow in a coronary vascular tree of a patient having the following method steps:

a) recording a first set of X-ray projection images of the vascular tree during various phases of a heart cycle while simultaneously recording a first ECG of the patient, the recording of the first set of X-ray projection images being performed at a plurality of projection angles;

b) reconstructing a three-dimensional structure of the vascular tree during the various phases of the heart cycle from the first set of X-ray projection images and splitting of the structure into a number of vascular segments;

c) recording of a second set of X-ray projection images of the vascular tree during or after administration of a contrast agent while a second ECG of the patient is being recorded, the recording of the second set of X-ray projection images being performed at a plurality of projection angles;

d) determining a time-dependent concentration of the contrast agent within a three-dimensional structure of the vascular tree as reconstructed in the method step b) by
  aa) assigning the X-ray projection images of the second set to a respective phase of the heart cycle using the recorded second ECG;
  bb) finding local image areas assigned to the vascular segments within the X-ray projection images of the second set corresponding to spatial positions of the vascular segments in the respective phase of the heart cycle according to the three-dimensional structure of the vascular tree;
  cc) determining the concentration of the contrast agent within the vascular segments by evaluating an X-ray absorption within the local image areas found in the method step bb);
e) generating a visualization of flow of the contrast agent through the three-dimensional structure of the vascular tree according to a time-dependent concentration of the contrast agent determined in method step d).

9. The X-ray imaging method as claimed in claim 8, wherein the second set of X-ray projection images is recorded during or after the administration of the contrast agent, while the vascular tree fills with the contrast agent and then the first set of X-ray projection images is recorded after the vascular tree is completely filled with the contrast agent.

10. The X-ray imaging method as claimed in claim 8, wherein the recording of at least one of the first and second set of X-ray projection images is effected using continuous rotation X-ray imaging at a plurality of projection angles.

11. The X-ray imaging method as claimed in claim 8, wherein a computer-aided modeling of the vascular tree, with elimination of other anatomical structures contained in the first set of X-ray projection images, is effected to reconstruct the three-dimensional structure in method step b).

* * * * *